United States Patent [19]

Maier

[11] Patent Number: 5,013,559
[45] Date of Patent: * May 7, 1991

[54] MICROBICIDES

[75] Inventor: Ludwig Maier, Arlesheim, Switzerland

[73] Assignee: Ciba-Geigy Corporation, Ardsley, N.Y.

[*] Notice: The portion of the term of this patent subsequent to Aug. 22, 2006 has been disclaimed.

[21] Appl. No.: 352,240

[22] Filed: May 15, 1989

Related U.S. Application Data

[63] Continuation of Ser. No. 131,710, Dec. 11, 1987, Pat. No. 4,859,466.

[30] Foreign Application Priority Data

Dec. 23, 1986 [CH] Switzerland .......................... 5202/86

[51] Int. Cl.⁵ ............................................ A01N 59/26
[52] U.S. Cl. .................................................. 424/605
[58] Field of Search .......................................... 424/605

[56] References Cited

PUBLICATIONS

L. Amat. (Compt. Rend.) 106 (1888), 1400.
L. Amat. (Compt. Rend.) 108 (1889), 1056.
Kiehl et al., J. Amer. Chem. Soc. 60(1938) pp. 47–49.

*Primary Examiner*—Allen J. Robinson
*Attorney, Agent, or Firm*—George R. Dohmann; Edward McC. Roberts; Kevin T. Mansfield

[57] ABSTRACT

The invention relates to salts of the pyrophosphorus acid of formula I

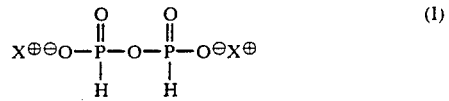

wherein $X^{\oplus}$ is a cation equivalent selected from the group consisting of sodium, potassium, lithium, beryllium, magnesium, aluminum, zinc, manganese, copper and $NH_4$, to the preparation thereof and to novel compounds of formula I, to the use of compounds of formula I as microbicides and as seed dressing agents.

3 Claims, No Drawings

MICROBICIDES

This is a continuation of application Ser. No. 131,710 filed on Dec. 11, 1987, now U.S. Pat. No. 4,859,466.

The present invention relates to microbicidally active salts of pyrophosphorous acid, to the preparation thereof, to microbicidal compositions, and to novel salts of pyrophosphorous acid.

It is known from U.S. Pat. No. 4,075,324 that certain salts of phosphorous acid are fungicidally active. These salts are not entirely satisfactory as regards their efficacy and duration of action.

It has now been found that salts of pyrophosphorous acid have enhanced microbicidal activity.

Specifically, the invention relates to salts of the pyrophosphorous acid of formula I

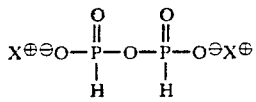

wherein $X^\oplus$ is a cation equivalent selected from the group consisting of sodium, potassium, lithium, beryllium, magnesium, aluminium, zinc, manganese, copper and $NH_4$.

Preferred plant microbicides are dilithium pyrophosphite and, most particularly, disodium pyrophosphite.

So far only a few salts of pyrophosphorous acid are known from the literature. For example, L. Amat (Compt. Rend. 106, (1888), 1400) describes the formation of disodium pyrophosphite by heating monosodium phosphite to 160° C. Similar results are reported respecting the potassium, rubidium and cesium salts (L. Amat, Compt. Rend. 108 (1889), 1056). These results are contradicted by Payne (J. Inorg. Nucl. Chem 26 (1964), 2103). According to investigations made by Rammelsberg (Pogg. Ann. (1867) 131, 263, 376; 132, 488; Ber. (1868) 1, 186), manganese, barium and calcium pyrophosphite cannot be prepared by heating the corresponding phosphites.

Kiehl et al. (J. Amer. Chem. Soc. 60(1938), 47) report on the preparation of diammonium pyrophosphite by heating monoammonium phosphite to 100°-120° C.

More recent publications relate to spectroscopic investigations of disodium pyrophosphite (M. Baudler, Z. Naturf. 12b (1957), 347; W. McFarlane, J. Chem. Soc. A, 1968 1715). McFarlane too reports that the product obtained by the process of Amat (vide supra) still contains appreciable amounts of starting materials.

Our own investigations show that it is not possible to prepare the salts of pyrophosphorous acid in sufficient purity by the processes known from the literature discussed above. Thus only a 1:1 mixture of monosodium phosphite and disodium pyrophosphite is obtained after heating monosodium phosphite for 10 hours to 160° C. (at 0.02 torr) by the process of Amat (vide supra). Likewise, after heating monoammonium phosphite for 39 hours to 120° C., no diammonium pyrophosphite is found, contrary to the findings of Kiehl. However, on heating under vacuum (0.02 torr) to 110° C., the formation of a novel hemi-salt in accordance with the following equation can be observed:

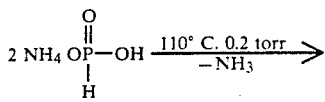

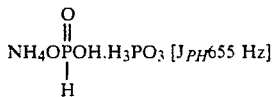

This hemi-salt remains unchanged after heating for 62 hours to 125° C. under vacuum.

The results of our own investigations as well as references in the literature indicate that, so far, no generally applicable process for the preparation of salts of pyrophosphorous acid is available.

Accordingly, it is a further object of this invention to provide processes for the preparation of salts of pyrophosphorous acid. This object is achieved by means of a process for the preparation of salts of the pyrophosphorous acid of formula.

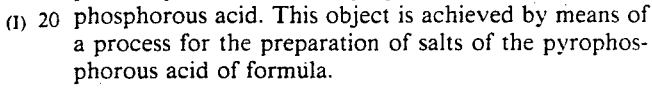

wherein $X^\oplus$ is a cation equivalent selected from the group consisting of sodium, potassium, lithium, beryllium, magnesium, aluminium, zinc, manganese, copper and $NH_4$, which process comprises dehydrating a salt of the phosphorous acid of formula II

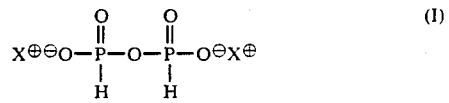

wherein $X^\oplus$ is as previously defined, at 80° to 280° C. in suspension, and removing the water formed during the reaction by appropriate measures.

It has been found expedient to comminute the phosphite used as educt as finely as possible so that it can be suspended in a liquid which boils in the indicated temperature range. As the reaction proceeds, the suspended solid can cake. The caked material should then be finely crushed.

The water formed during the condensation can be conveniently removed from the reaction mixture by azeotropic distillation by a liquid which is water-immiscible or which is miscible with water to only a limited degree.

The azeotropic distillation of water formed during condensation reaction is a method generally known in preparative chemistry. Surprisingly, by heating salts of the phosphorous acid of formula II in liquids which form an azeotrope with water in the vapour phase it is possible to obtain the salts of the pyrophosphorous acid of formula I in almost quantitative yield, which salts are now available in sufficient purity almost 100 years after the disodium salt was first described.

The invention further relates to the compounds of formula I, especially disodium pyrophosphite, obtained by the above described process as novel compounds in a purity which is markedly superior to that of the prior art. First and foremost, the invention relates to a disodium pyrophosphite, $Na_2H_2P_2O_5$, and a dilithium pyrophosphite. $Li_2H_2P_2O_5$, in at least 99.0% purity.

The invention also relates to the novel compounds of formula I. wherein X is lithium, beryllium, magnesium, calcium, barium, aluminium, manganese, zinc and copper(I) or copper(II).

The liquid employed as azeotropic entrainer can be selected from a wide range of known solvents or mixtures of solvents that form azeotropes with water and which boil in the indicated temperature range. Typical examples of such solvents are high boiling hydrocarbons such as dodecane, naphthalene, decalin, tetralin, and halogenated hydrocarbons such as benzal dichloride, benzotrichloride, chlorobenzyl chloride, dibromobenzene, chlorobromobenzene, as well as further high boiling solvents such as esters containing not less than 9 carbon atoms. e.g. ethyl benzoate or octyl formate (list of suitable solvents e.g. in CRC Handbook of Chemistry and Physics, 52nd Ed., Cranwood, Ohio, 1971, Azeotropes, pp. D1–D44.

The reaction involving compounds of formulae I and II. wherein X is ammonia, is conveniently carried out in the temperature range from 80° to 140° C., whereas a temperature range from 180° to 250° C. is preferred for the other salts of phosphorous acid.

Suitable entrainers in the case of diammonium pyrophosphite are those solvents which boil in the range from 80° to 140° C.

Preferred solvents for the other compounds of formula I, wherein X is an alkali, alkaline earth, aluminium, manganese, zinc or copper ion. are those which boil in the range from 180° to 250° C.

Within the prescribed temperature ranges, any solvents or mixtures of solvents may be chosen.

Particularly suitable solvents for the temperature range from 80° to 140° C. are 1,1,2-trichloroethane or toluene and, for the temperature range from 180° to 250° C., 1,2,4-trichlorobenzene.

If X is a monovalent cation, the pyrophosphites of formula I are soluble in water; but if X is a cation equivalent of a divalent or trivalent cation, the corresponding salts are sparingly soluble or insoluble in water.

Whereas the water-soluble compounds of formula I can be formulated to liquid as well as to solid forms, the compounds which are sparingly soluble or insoluble in water are preferably formulated to solid forms, for example to dusts, wettable powders or suspension concentrates.

The compounds of formula I of this invention have very useful curative, preventive and systemic properties for protecting cultivated plants. With these compounds of formula I it is possible to inhibit or destroy the microorganisms which occur in plants or parts of plants (fruit, blossoms, leaves, stems, tubers, roots) in different crops of useful plants.

The compounds of formula I are effective against the phytopathogenic fungi belonging to the following classes: Ascomycetes (e.g. Venturia, Podosphaera, Erysiphe, Monilinia, Uncinula): Basidiomycetes (e.g. the genera Hemileia, Rhizoctonia, Puccinia); *Fungi imperfecti* (e.g. Botrytis, Helminthosporium, Fusarium, Septoria, Cercospora, Alternaria and, especially, Pyricularia). The compounds of formula I are especially effective against the Oomycetes belonging to the class of the Phycomycetes, e.g. Phytophthora, Peronospora, Pseudoperonospara, Pythium or Plasmopara. They can also be used as seed dressing agents for protecting seeds (fruit, tubers, grains) and plant cuttings against fungus infections as well as against phytopathogenic fungi which occur in the soil. The combinations of the invention are especially well tolerated by plants and they are ecologically non-harmful. Pyrophosphorous acid and its salts are converted in the course of time into phosphates and therefore act later as fertilisers when applied to the soil. This applies most particularly to disodium pyrophosphite, which is degraded to disodium phosphate.

Without implying any limitation, target crops to be protected within the scope of the present invention comprise e.g. the following species of plants:

cereals (wheat, barley, rye, oats, rice, sorghum and related gramineae, e.g. turf), beet (sugar beet and fodder beet), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and condifers).

The compounds of formula I are applied to the crop area or plant to be treated, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

To broaden the activity spectrum it is also possible to add further microbicides, e.g. dithiocarbamates such as zineb, maneb and, preferably, mancozeb.

A preferred method of applying a compound of formula I is application to the growing parts of plants, especially the leaves (foliar application). The number of applications and the rate of application depend on the biological and climatic life conditions of the pathogen. However, the active ingredient can also penetrate the plant through the roots via the soil by drenching the locus of the plant with a liquid formulation, or by applying the compounds in solid form to the soil, e.g. in granular form (soil application). The compounds of formula I may also be applied to seeds (coating) by impregnating the seeds either with a liquid formulation of the active ingredient or coating them with a combined formulation. In special cases, further types of application are also possible, e.g. selective treatment of the buds or infructescences.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 100 g to 6 kg a.i./ha, most preferably from 100 g to 2000 g a.i./ha.

The formulations are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins. Examples of synthetic phospholipids are dioctanoylphosphatidyl choline and dipalmitoylphosphatidyl choline.

Depending on the nature of the compounds of formula I to be formulated, suitable surface-active compounds are nonionic, cationic and/or anionic sufactants having good emulsifying, dispersing and wetting properties. The term "surfactants" will also be understood as comprising mixtures of surfactants.

Furthermore, the present invention also embraces a method of treating plant diseases, which comprises applying the compounds of formula I and the novel compositions containing them to the locus already infected or in danger of infection.

| Wettable powders | (a) | (b) | (c) |
| --- | --- | --- | --- |
| compound of formula I | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

| Emulsifiable concentrate | |
| --- | --- |
| compound of formula I | 10% |
| octylphenol polyethlene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| Dusts | (a) | (b) |
| --- | --- | --- |
| compound of formula I | 5% | 8% |
| talcum | 95% | — |
| kaolin | — | 92% |

Ready-for-use dusts are obtained by mixing the active ingredient with the carriers, and grinding the mixture in a suitable mill.

| Extruder granulate | |
| --- | --- |
| compound of formula I | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Coated granulate | |
| --- | --- |
| compound of formula I | 3% |
| polyethylene glycol 200 (mol wt.) | 3% |
| kaolin | 94% |

The finely ground active ingredient is uniformly applied, in a mixer, to the kaolin moistened with polyethylene glycol. Non-dusty coated granulates are obtained in this manner.

The invention is illustrated by the following Examples.

PREPARATORY EXAMPLES

P1.1: Synthesis of Disodium Pyrophosphite without a Solvent 15.8 g (0.152 mole) of $NaH_2PO_3$ are heated at 200° C. under vacuum for 17 hours. The heavily caked substance is pulverised repeatedly during this time. Subsequently 14.02 g (97.1% of theory, based on pyrophosphite) of a white product are isolated. Analysis by $^{31}P$-NMR spectroscopy shows the product to consist of 91% of the title compound of formula

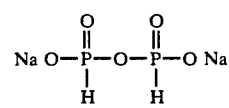

($^{31}P$-NMR ($D_2O$) $\delta = 4.89$ ppm, $J_{PH} = 666$ Hz) and 9% of the starting compound of formula

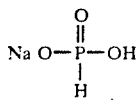

(3¹

P-NMR (D₂O) δ=4.15 pmm, J$_{PH}$=599 Hz).

Compared with this prior art process, which results in a very impure final product, the process of this invention for dehydrating a phosphite in suspension makes it possible to obtain a very pure pyrophosphite, as will be described in the following Examples P1.2, P2, P3, P4.2 and P5.

1.2: Synthesis of Disodium Pyrophosphite using an Azeotropic Entrainer

With stirring, 221 g (2.125 moles) of NaH₂PO₃ and 400 ml of 1,2,4-trichlorobenzene are heated to the boil for 17 hours in an apparatus equipped with a water separator. During this time the reaction mass cakes and is removed from time to time and pulverised. After cooling, the product is isolated by filtration affording 201 g (99.6%) of the title compound of formula

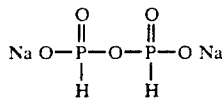

of m.p. >300° C.

³¹P-NMR (D₂O) δ=4.89 ppm, J$_{PH}$=666 Hz; ¹H-NMR (D₂O): δ=7.1 ppm, J$_{PH}$=661 Hz.

H₂P₂O₅Na₂ (189,95): theory: P 32.61%, Na 24.21%. found: P 32.4%, Na 24.5%.

P.2: Synthesis of Dilithium Pyrophosphite

In accordance with the procedure of Example P1.2, heating LiH₂PO₃ in 1,2,4-trichlorobenzene for 7 hours gives the title compound of formula

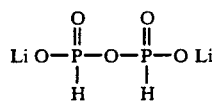

in quantitative yield as a solid with a melting point of >300° C.

³¹P NMR (H₂O) δ=4.9 ppm.

¹H NMR (D₂O) δ=6.94 ppm, J$_{PH}$=673 Hz.

P3: Synthesis of Magnesium Pyrophosphite

In accordance with the procedure described in Example P1.2, heating [Mg]₀.₅H₂PO₃ in 1,2,4-trichlorobenzene for 22 hours give the title compound of formula

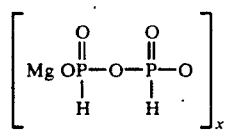

as a sparingly soluble solid.

P4: Synthesis of Aluminium Pyrophosphite

P4.1: Synthesis of Aluminium Phosphite

To a solution of 30.3 g (0.369 mole) of phosphorous acid in 100 ml of water are added 20 g (0.123 mole) of aluminium triethanolate. After the exothermic reaction has subsided, the reaction mixture is left for 14 hours at room temperature and thereafter evaporated to dryness, affording 32.9 g (99%) of the title compound of formula

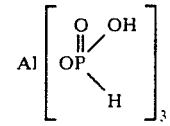

as a solid with a melting point of 195° C. (dec.).

P4.2: Synthesis of Aluminium Pyrophosphite 8.0 g (0.03 mole) of aluminium phosphite are heated in 1,2,4-trichlorobenzene to the boil for 16 hours on a water separator. The 1,2,4-trichlorobenzene is removed by decantation and the residue is suspended in dichloromethane. The suspension is filtered and the filter residue is dried, affording 5.63 g (75.3%) of the title compound of formula

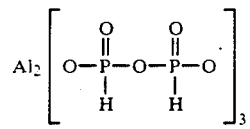

as a water-insoluble solid with a melting point >300° C.

P5: Synthesis of Diammonium Pyrophosphite

Ammonium phosphite is left for 3 days in boiling 1,1,2-trichloroethane in an apparatus equipped with a water separator. The title compound of formula

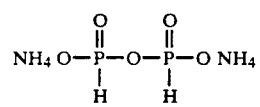

is isolated in 80% yield together with residual amounts of ammonium phosphite.

¹H-NMR (D₂O) δ=7.4 ppm (PH, J$_{PH}$=676 Hz; δ=5.8 ppm (NH₄).

Following the procedures described in the foregoing Examples, the following salts of pyrophosphorous acid can be obtained:

| | |
|---|---|
| dipotassium pyrophosphite | (K₂H₂P₂O₅) |
| calcium pyrophosphite | (CaH₂P₂O₅) |
| copper(II) pyrophosphite | (CuH₂P₂O₅) |
| zinc(II) pyrophosphite | (Zn H₂P₂O₅) |
| copper(I) pyrophosphite | (Cu₂H₂P₂O₅) |
| barium pyrophosphite | (BaH₂P₂O₅) |
| manganese pyrophosphite | (MnH₂P₂O₅) |

BIOLOGICAL EXAMPLES

B1: Plasmapara Viticola on Vines

Five-week-old vine seedlings are sprayed with a spray mixture (0.02% active ingredient) prepared from a formulation of the test compound and infected one day later with a sporangia suspension (20,000 sporangias/ml) of *P. viticola*. The infected plants are then incubated at 20° C. in a greenhouse. A 14 hour incubation phase at 100% relative humidity is followed by incubation for 4 days at 75-80% relative humidity and, finally, to induce fungus sporulation, for one night at 100% relative humidity. Evaluation of fungus attack is made after the 6 day incubation (0-5% = complete activity).

| compound | fungus attack |
| --- | --- |
| $MgH_2P_2O_5$ | <20% |
| $Li_2H_2P_2O_5$ | 0-5% |
| $Na_2H_2P_2O_5$ | 0-5% |
| *$Na_2H_2P_2O_5$ + mancozeb | 0-5% |

*The spray mixture contained 150 g/100 liters of $Na_2H_2P_2O_5$ and 120 g/100 liters of mancozeb and was likewise tested in a concentration 0.2%.

B2: Activity Against Phytophtora Infestans on Tomato Plants Residul-Protective Activity After 3 week growth, tomato plants are sprayed with a spray mixture (0.2% of active ingredient) prepared as described above from a wettable powder formulation of the test compound. After 24 hours the treated plants are infected with a sporangia suspension of the fungus. Evaluation of fungus attack is made after incubation of the infected plants for 5 days at 90-100% relative humidity and 20° C.

| compound | fungus attack |
| --- | --- |
| $Li_2H_2P_2O_5$ | 5-20% |
| $Na_2H_2P_2O_5$ | 5-10% |

What is claimed is:

1. A fungicidal composition for protecting plants containing a fungicidally effective amount of a salt of the pyrophosphorous acid of formula I

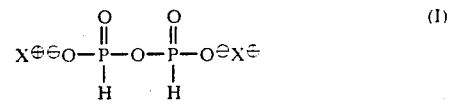

wherein $X^\oplus$ is a cation equivalent selected from the group consisting of sodium, potassium, lithium, beryllium, magnesium, aluminium, zinc, manganese, copper and $NH_4$, together with a suitable carrier therefor and a surfactant.

2. A composition according to claim 1, which contains dilithium pyrophosphite.

3. A composition according to claim 1, which contains disodium pyrophosphite.

* * * * *